(12) United States Patent
Felix

(10) Patent No.: US 7,691,129 B2
(45) Date of Patent: Apr. 6, 2010

(54) SPINAL STABILIZING SYSTEM

(76) Inventor: Brent A. Felix, 2911 E. Little Cottonwood Rd., Sandy, UT (US) 84092

( * ) Notice: Subject to any disclaimer, the term of this patent is extended or adjusted under 35 U.S.C. 154(b) by 774 days.

(21) Appl. No.: 11/254,634

(22) Filed: Oct. 20, 2005

(65) Prior Publication Data
US 2006/0089644 A1   Apr. 27, 2006

Related U.S. Application Data

(60) Provisional application No. 60/623,007, filed on Oct. 27, 2004, provisional application No. 60/623,008, filed on Oct. 27, 2004, provisional application No. 60/623,009, filed on Oct. 27, 2004, provisional application No. 60/623,010, filed on Oct. 27, 2004.

(51) Int. Cl.
*A61B 17/56* (2006.01)
*A61B 17/58* (2006.01)
*A61B 17/68* (2006.01)

(52) U.S. Cl. .................. 606/246; 606/60; 606/250; 606/254

(58) Field of Classification Search .............. 606/61, 606/72, 73, 60, 86 A, 246, 250, 254–260, 606/270, 279, 300, 914
See application file for complete search history.

(56) References Cited

U.S. PATENT DOCUMENTS

| | | | |
|---|---|---|---|
| 5,466,237 A | | 11/1995 | Byrd, III et al. |
| 5,474,555 A | | 12/1995 | Puno et al. |
| 5,941,885 A | * | 8/1999 | Jackson ............ 606/104 |
| 5,947,965 A | * | 9/1999 | Bryan ............... 606/61 |
| 5,989,254 A | * | 11/1999 | Katz ................ 606/308 |
| 6,063,090 A | | 5/2000 | Schlapher |
| 6,113,600 A | * | 9/2000 | Drummond et al. ... 606/252 |
| 6,113,601 A | * | 9/2000 | Tatar ................ 606/266 |
| 6,248,105 B1 | | 6/2001 | Schlapher et al. |
| 6,280,442 B1 | | 8/2001 | Barker et al. |
| 6,371,957 B1 | | 4/2002 | Amrein et al. |
| 6,471,705 B1 | | 10/2002 | Biedermann et al. |
| 6,565,567 B1 | | 5/2003 | Haider |

(Continued)

OTHER PUBLICATIONS

Biologic & Structural Innovation, *VLS System Variable Locking Screw*, Interpore Cross International, 2001.

(Continued)

*Primary Examiner*—Thomas C Barrett
*Assistant Examiner*—Sameh Boles
(74) *Attorney, Agent, or Firm*—Workman Nydegger

(57) ABSTRACT

A spinal stabilizing system includes a collar having a tubular sidewall with an interior surface and an exterior surface, the interior surface at least partially bounding a longitudinal passage extending therethrough. A shoulder radially inwardly projects from a second end of the sidewall so as to at last partially encircle the longitudinal passage. A pair of spaced apart channels transversely extend through the sidewall at the first end thereof. The system further includes a screw having a threaded portion and an enlarged head mounted on the end thereof, the head of the screw resting against the shoulder of the collar so that the head can pivot on the shoulder, a locking slot being formed on the head of the screw. A pin is secured to the collar and projects into the locking slot on the head of the screw such rotation of the collar facilitates rotation of the screw.

36 Claims, 14 Drawing Sheets

U.S. PATENT DOCUMENTS

| | | | |
|---|---|---|---|
| 6,641,586 B2 | 11/2003 | Varieur | |
| 6,660,004 B2 | 12/2003 | Barker et al. | |
| 6,740,086 B2 | 5/2004 | Richelsoph | |
| 7,144,396 B2 * | 12/2006 | Shluzas | 606/61 |
| 7,322,981 B2 * | 1/2008 | Jackson | 606/61 |
| 2006/0085072 A1 | 4/2006 | Funk et al. | |
| 2007/0043355 A1 * | 2/2007 | Bette et al. | 606/61 |

OTHER PUBLICATIONS

EBI Spine Systems, *EBI Ωmega21 Spinal Fixation System, Surgical Technique*, published at least as early as Dec. 14, 1999.

Synthes Spine, *Click'X Top Loading System, Technique Guide*, 2003.

Biologic & Structural Innovation, *Synergy IQ, Low Back Surgical Technique*, Interpore Cross International, 2003.

* cited by examiner

SPINAL STABILIZING SYSTEM

CROSS-REFERENCE TO RELATED APPLICATIONS

The present application claims priority to U.S. Provisional Application Nos. 60/623,007, filed Oct. 27, 2004; 60/623,008, filed Oct. 27, 2004; 60/623,009, filed Oct. 27, 2004; and 60/623,010, filed Oct. 27, 2004, which applications are incorporated herein by specific reference.

BACKGROUND OF THE INVENTION

1. The Field of the Invention

The present invention relates to systems and methods for stabilizing a portion of a spine. More specifically, the invention relates to anchors and related components that are selectively mounted on a spine for stabilizing the spine.

2. The Relevant Technology

There are many surgical procedures and treatments that require the immobilization of a portion of the spine. For example, vertebral fusion is a medical procedure where adjacent vertebrae of the spine are fused together. As part of this procedure, a mechanical stabilizing system is implanted in the patient which immobilizes the adjacent vertebrae. Such stabilizing systems can also be used in the treatment of spinal trauma and spinal curvature such as scoliosis.

A typical spinal stabilizing system includes, in part, a pair of anchors and a rigid rod that extends between the anchors. The anchors are fixed to the adjacent vertebra such that when the rod is connected to the anchors, the adjacent vertebra become immobilized. A typical anchor includes a cylindrical tubular body having a longitudinal passage extending therethrough and a transverse passage extending therethrough. The exterior surface of the tubular body is round and has threads thereon to receive a nut.

The anchor also includes an elongated screw having an enlarged head formed on one end thereof. The head has a polygonal socket formed thereon in alignment with the longitudinal axis of the screw. The enlarged head of the screw is seated within the tubular body such that the tubular body can freely rotate and pivot relative to the screw. Once the screws are screwed into the corresponding vertebra, the rod is positioned within the transverse passage of each tubular body. A nut is then screwed onto the exterior of the tubular body. The nut biases the rod against the head of the screw so as to rigidly secure the rod to the anchor.

Although spinal stabilizing systems are commonly used, conventional systems have a number of shortcomings. For example, mounting of the screw into the bone requires a thin elongated driver that mates with the polygonal socket on the head of the screw. Conventional drivers can be difficult and awkward to use resulting in misalignment of the screws. Furthermore, on occasion it is necessary to remove a screw after it has been implanted for an extended period of time. While the screw is implanted, however, tissue and/or bone typically grows over the head of the screw, thereby making is difficult to access the screw and couple the driver with the screw.

In addition, because the socket is formed on the top of the head of the screw, the top surface of the head is flat. During use, the rod rests on top of the head of the screw. However, the tubular body is often pivoted relative to the longitudinal axis of the screw so that the rod can be received within the transverse passage. As a result of the tubular body being pivoted, the rod often rests irregularly on the corner of the flat surface formed on the head of the screw. This irregular seating of the rod on the head of the screw can produce a weak connection, produce undesired pivoting of the screw or tubular body, and/or produce unwanted stress on the spine.

Furthermore, as the nut is tightened on the tubular body, the remainder of the anchor needs to be stabilized so that undue loads are not applied to the spine. To accomplish this, an anti-torque device is passed over the tubular body so as to engage only the rod passing therethrough. An opposing force is then applied by the anti-torque device to the rod as the nut is tightened onto the tubular body, thereby minimizing undue stress on the spine. One difficulty with this approach, however, is that the rod is often disposed directly on or adjacent to the bone and/or tissue. As such, it is often difficult and time consuming to adequately place the anti-torque device over the rod.

Accordingly, it would be beneficial to have spinal stabilizing systems that address some or all of the foregoing shortcomings.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
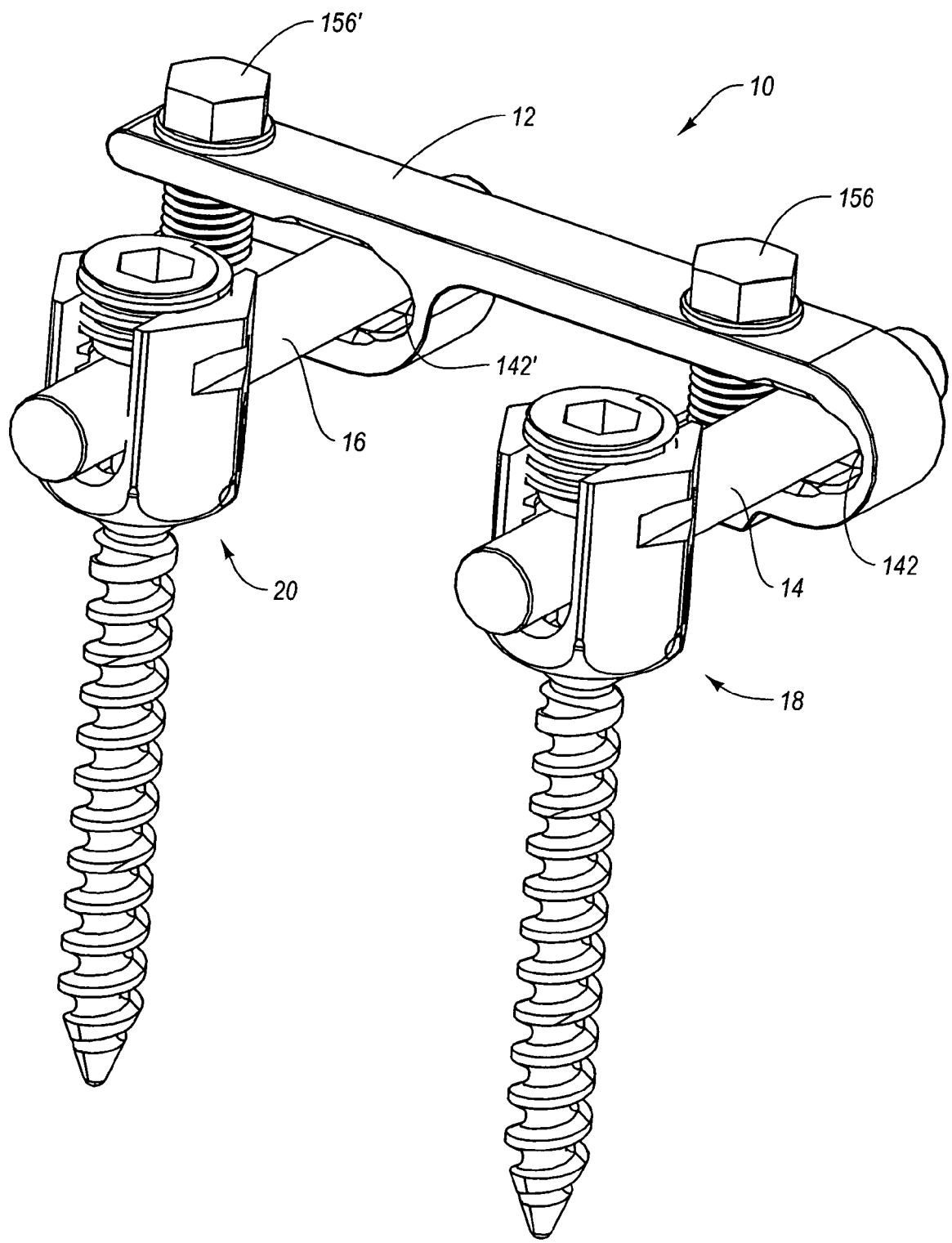
FIG. 1 is a perspective view of one embodiment of a spinal stabilizing system.

Depicted in FIG. 1 is one embodiment of a spinal stabilizing system 10 incorporating features of the present invention. In one embodiment, spinal stabilizing system 10 can be used for stabilizing adjacent vertebrae of a spin as part of a procedure for fusing together the adjacent vertebrae. Spinal stabilizing system 10 can also be used for stabilizing a series of consecutive vertebrae for manipulation of the spine to correct spinal deformities such as scoliosis. It is appreciated that spinal stabilizing system 10 and/or discrete elements thereof can also be used in other procedures for anchoring, manipulating, and/or stabilizing various bones.

Spinal stabilizing system 10 generally comprises a cross link 12 having a first stabilizing rod 14 and a second stabilizing rod 16 mounted on and projecting therefrom. A first anchor assembly 18 is mounted on first stabilizing rod 14 while a second anchor assembly 20 is mounted on second stabilizing rod 16. Anchor assemblies 18 and 20 are identical. Thus, all disclosure with regard to first anchor assembly 18 is also applicable to second anchor assembly 20.

Figure 2:
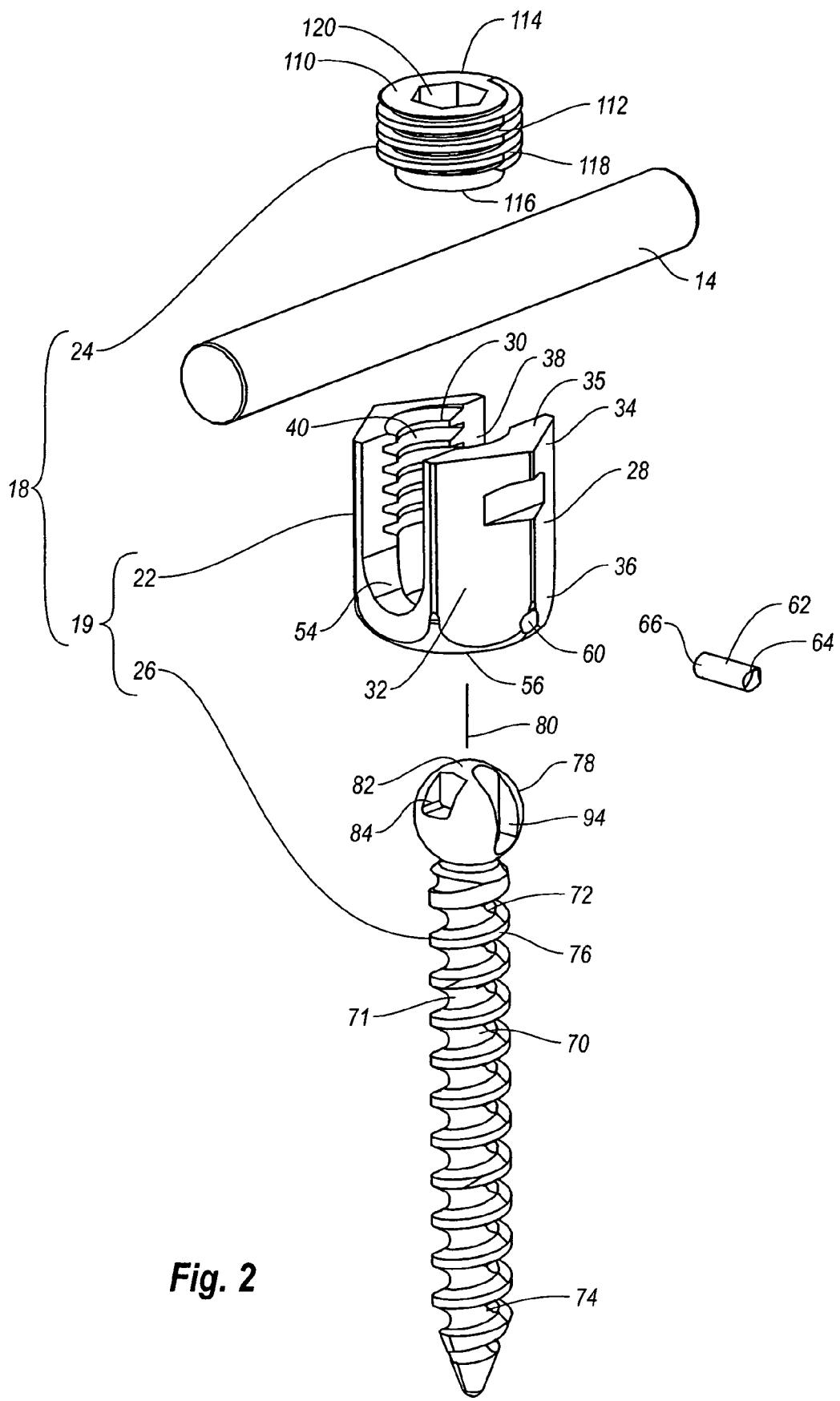
FIG. 2 is an exploded perspective view of an anchor assembly of the spinal stabilizing system depicted in FIG. 1.

As depicted in FIG. 2, anchor assembly 18 comprises an anchor 19 on which a fastener 24 selectively engages. Anchor 19 comprises an elongated screw 26, a collar 22 pivotally mounted on screw 26, and a pin 62 that extends between screw 26 and collar 22. Collar 22 comprises a tubular side wall 28 having an interior surface 30 and an exterior surface 32 that each extend between a first end 34 and an opposing second end 36. First end 34 terminates at a terminal end face 35. Interior surface 30 bounds a longitudinal passage 38 that longitudinally extends through collar 22. Internal threads 40 are formed on interior surface 30 at or toward first end 34.

Figure 3:
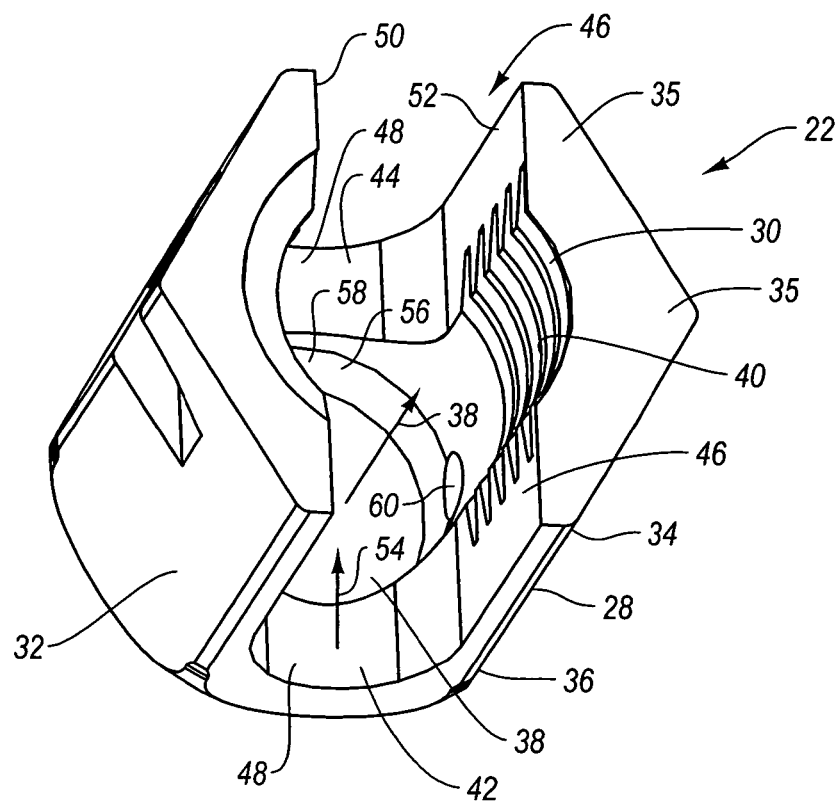
FIG. 3 is a perspective view of the collar of the anchor assembly shown in FIG. 2.
Figure 9:
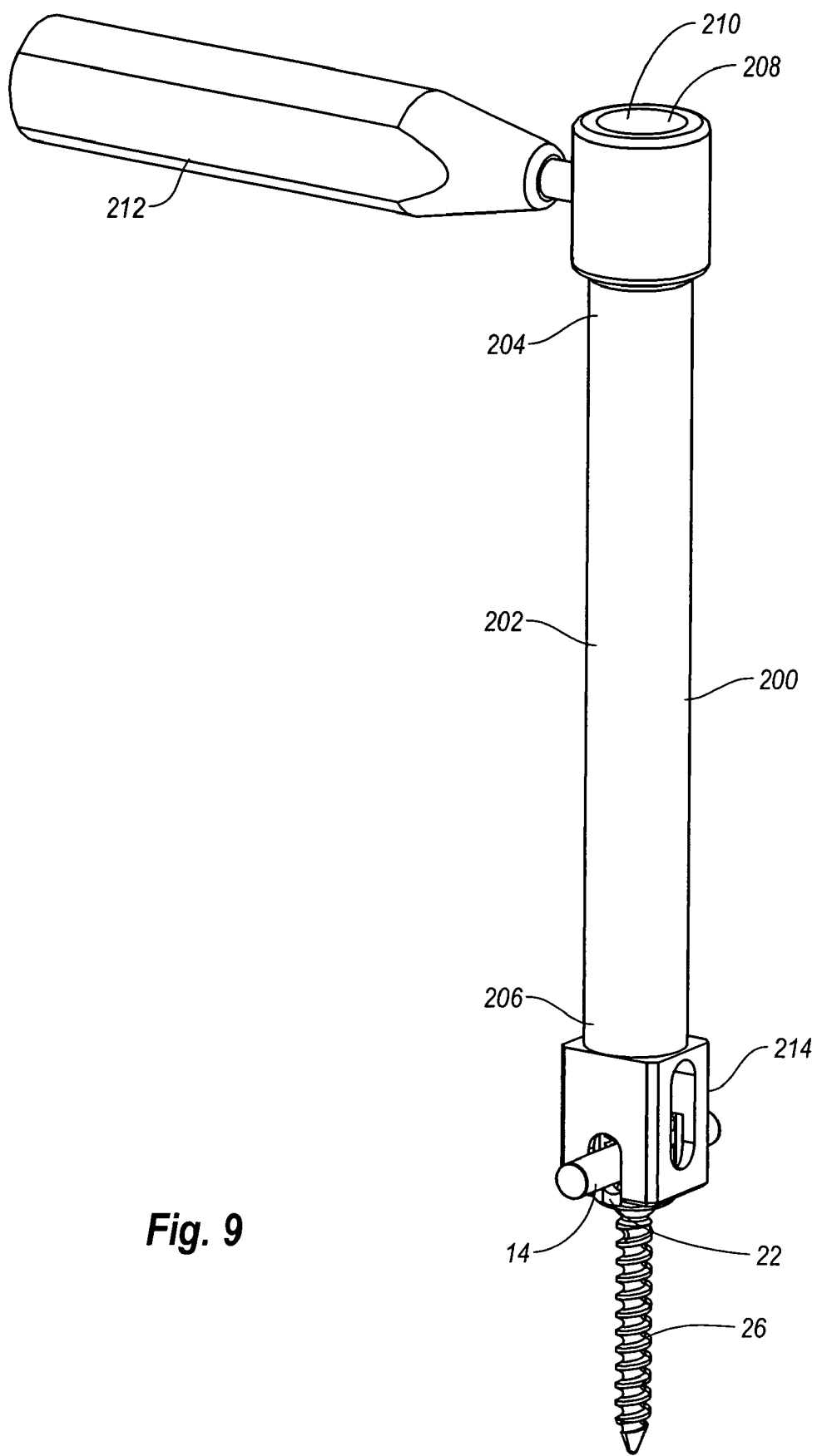
FIG. 9 is a perspective view of an anti-torque device coupling with the anchor assembly of FIG. 1.
Figure 10:
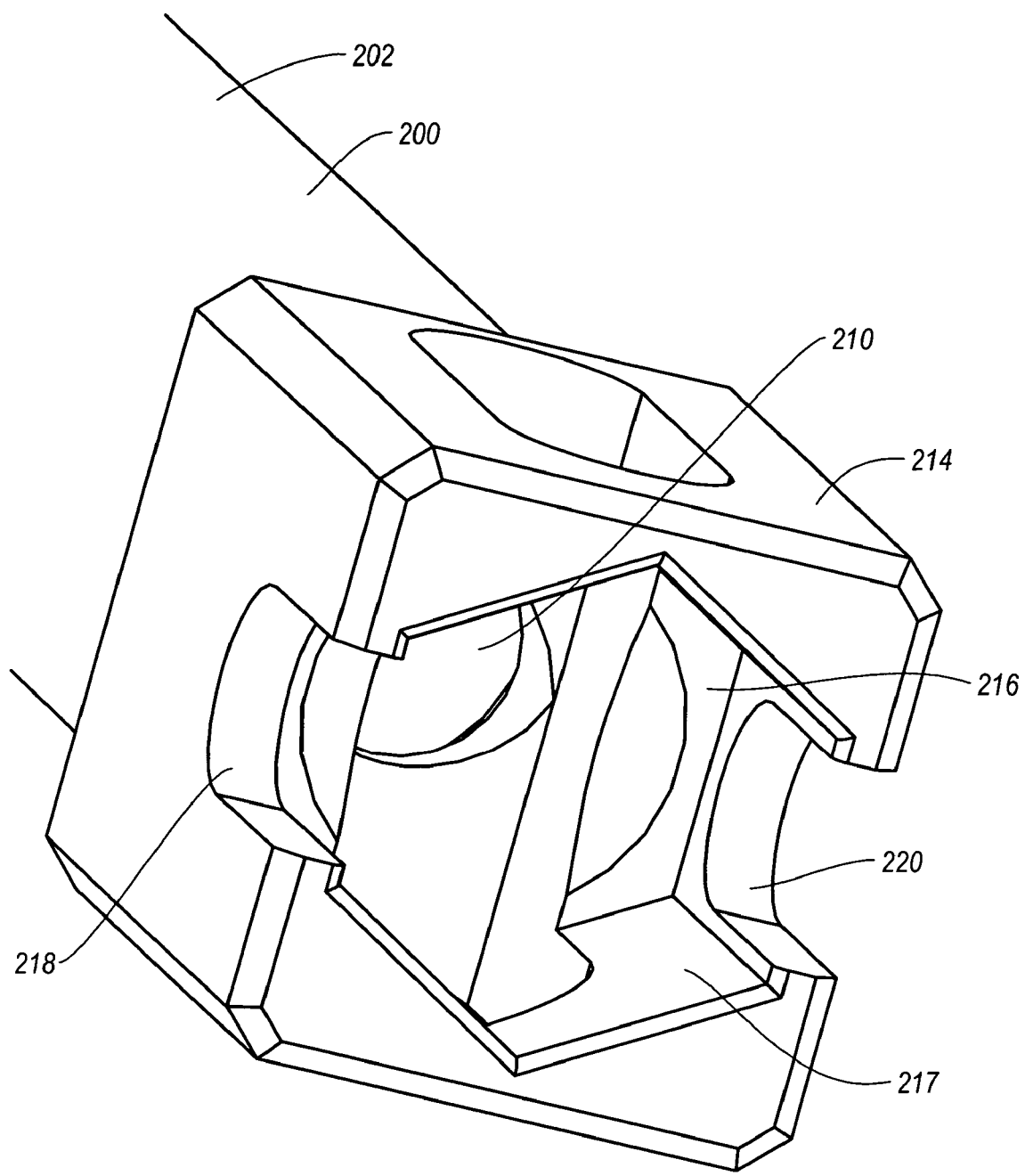
FIG. 10 is a perspective end view of the anti-torque device shown in FIG. 9.

As perhaps best depicted in FIG. 3, exterior surface 32 of side wall 28 has a substantially polygonal transverse cross section. As a result of having a polygonal configuration, an engagement tool, such as depicted in FIGS. 9 and 10, can easily engage exterior surface 32 of collar 22 so as to either rigidly hold collar 22 or facilitate selective rotation of collar 22. In the embodiment depicted, exterior surface 32 has a six sided polygonal configuration. In alternative embodiments, it is appreciated that exterior surface 32 can have a variety of alternative polygonal configurations such as four sided, eight sided, twelve sided, or any other polygonal configuration. In still other embodiments, exterior surface 32 can have any non-circular transverse cross section. As a result of being non-circular, a corresponding socket of an engagement tool can be placed over first end 34 of collar 22 to mechanically engage collar 22.

Furthermore, in the embodiment depicted the polygonal transverse cross section is substantially constant along the length of side wall 28. In an alternative embodiment the polygonal configuration need only extend along a length of side wall 28. The remainder of side wall 28 can be circular or any other desired configuration.

Side wall 28 is formed having a pair of channels 42 and 44 that are disposed on opposing sides of side wall 28 and that transversely extend through side wall 28. In the embodiment depicted, channels 42 and 44 each have a substantially U-shaped configuration. Each channel 42 and 44 has an open mouth 46 that extends through end face 35 and an opposing floor 48 that is rounded. As will be discussed below in greater detail, each channel 42 and 44 is configured so that stabilizing rod 14 can be received therein. In alternative embodiments, floor 48 need not be rounded but can be flat, V-shaped, or have other configurations. Each of channels 42 and 44 are also bounded by opposing side surfaces 50 and 52. Although side surfaces 50 and 52 are shown as being in substantially parallel alignment, in alternative embodiments side surfaces 50 and 52 can be designed to diverge or converge as they project away from floor 48. Other configurations can also be used. Channels 42 and 44 form a portion of a transverse passage that transversely extends through collar 22, as identified by arrow 54, so as to intersect with the longitudinal passage that also extends through collar 22, as identified by arrow 38.

As also depicted in FIG. 3, collar 22 further comprises a shoulder 56 that radially inwardly projects from second end 36 of side wall 28 so as to encircle longitudinal passage 38. Shoulder 56 has a tapered interior surface that forms an annular seat 58. As will be discussed below in greater detail, a portion of screw 26 rests against seat 58 so that collar 22 can pivot relative to screw 26. In alternative embodiments, seat 58 need not completely encircle passage 38. Seat 58 can also comprise two or more spaced apart portions. Finally, a pin hole 60 transversely extends through side wall 28 and/or shoulder 56 at second end 36 of side wall 50. Although not required, pin hole 60 is typically disposed orthogonal to transverse passage 54. As will also be discussed below in greater detail, pin hole 60 is adapted to receive pin 62 (FIG. 2) which has a first end 64 and an opposing second end 66.

Returning to FIG. 2, screw 26 comprises an elongated shaft 70 having an exterior surface 71 extending between a first end 72 and an opposing second end 74. A thread 76 helically encircles and radially outwardly projects from shaft 70 along the length thereof. In one embodiment one or more helical threads can be formed on shaft 70. Thread 76 can have a variety of different pitches and configurations, and, if desired, can be self-tapping.

Figure 4:
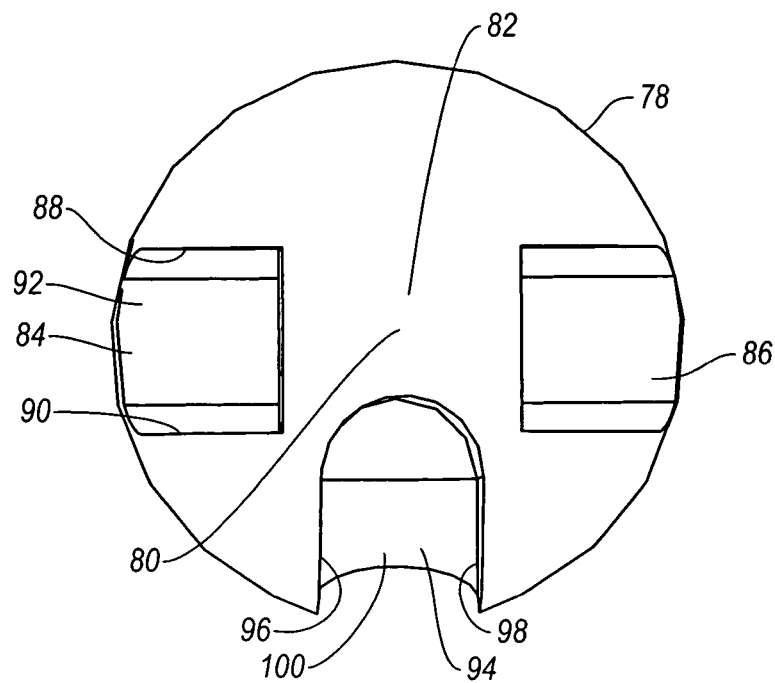
FIG. 4 is a top plan view of the screw of the anchor assembly shown in FIG. 2.

An enlarged head 78 is disposed on first end 72 of shaft 70. Although not required, in the embodiment depicted head 78 has a substantially spherical configuration. It is also noted that shaft 70 has a central longitudinal axis 80 extending therethrough which axis 80 passes through head 78. Head 78 has a rounded crown 82 in the form of a convex dome disposed on a side of head 78 opposite of shaft 70 and through which central longitudinal axis 80 extends. As depicted in FIG. 4, a pair of spaced apart engagement slots 84 and 86 is formed on opposing sides of head 78 at spaced apart locations from central longitudinal axis 80. Each engagement slot 84 and 86 has a pair of opposing inside faces 88 and 90 that are disposed in substantially parallel alignment and which extend down to a floor 92.

As shown in FIGS. 2 and 4, also formed on head 78 at a location spaced apart from central longitudinal axis 80 is an elongated locking slot 94. Locking slot 94 also has a pair of opposing inside faces 96 and 98 which extend to a floor 100. Although not required, inside faces 96 and 98 are shown as being disposed as substantially parallel alignment. In the embodiment depicted, locking slot 94 extends over half the length of head 78 while engagement slots 84 and 86 extend less than half the length of head 78. In alternative embodiments, however, engagement slots 84, 86 and locking slot 94 can be different lengths.

Figure 5:
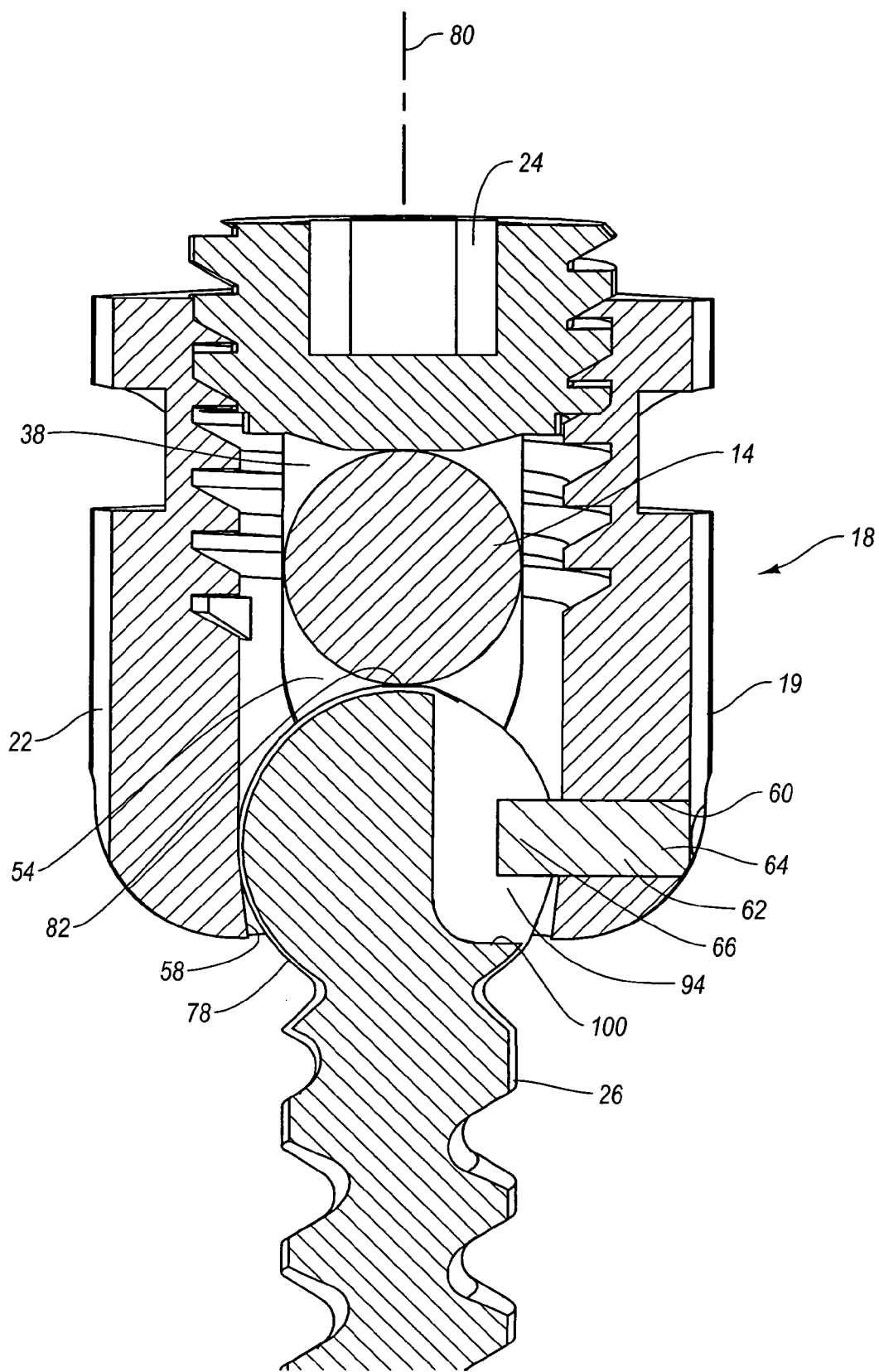
FIG. 5 is a cross sectional side view of the anchor assembly shown in FIG. 1.

Turning to FIG. 5, during assembly of anchor 19, second end 74 of screw 26 is passed down through longitudinal passage 38 of collar 22. Head 78 of screw 26, however, has a maximum diameter that is greater than the minimum diameter of longitudinal passage 38 extending through seat 58 of collar 22. As such, head 78 of screw 26 rests on seat 58 of collar 22 and is prevented from passing through longitudinal passage 38. As a result of the spherical configuration of head 78 and the tapered sloping of seat 58, head 78 can freely slide on seat 58 such that screw 26 and collar 22 can freely pivot relative to each other. Specifically, relative to longitudinal axis 80, collar 22 can pivot any 360° direction. The amount of pivot in one direction from longitudinal axis 80 is typically greater than 10° and more commonly greater than 15°. Other angles can also be formed.

Once screw 26 is seated within collar 22, pin 62 is advanced into pin hole 60. First end 64 of pin 62 is secured within pin hole 60 such as by welding, adhesive, press fit, or other mechanical engagements, such as threaded engagement. In this position, second end 66 of pin 62 projects into locking slot 94 of screw 26. It is noted that pin 62 is spaced apart above floor 100 of locking slot 94. As a result, screw 26 and collar 22 can continue to freely pivot relative to each other. However, because pin 62 extends over floor 100, head 78 is prevented from passing back up through collar 22. Pin 62 also functions to couple screw 26 and collar 22 together so that rotation of collar 22 also facilitates rotation of screw 26. As such, screw 26 can be implanted or removed by simply by rotating collar 22. In one embodiment of the present invention means are provided for locking screw 26 to collar 22 so that collar 22 can freely pivot on head 78 of screw 26 and so that rotation of collar 22 facilitates rotation of screw 26. On example of such means comprises pin 62 with corresponding locking slot 94. In alternative embodiments, it is appreciated that pin 62 can come in a variety of different configurations and can be mounted at a variety of different orientations and locations.

Returning to FIG. 2, stabilizing rod 14 typically has a substantially cylindrical configuration and is sized to fit within transverse passage 54 of collar 22. In one embodiment stabilizing rod 14 has a diameter in a range between about 3 mm to about 8 mm. However, in alternative embodiments, stabilizing rod 14 can have a variety of different diameters and can have other transverse cross sections such as polygonal, elliptical, irregular, or the like. However, having a circular transverse cross section provides for uniform engagement and seating with screw 26, fastener 24, and cross link 12. It is appreciated that stabilizing rod 14 can come in a variety of different lengths depending on its intended use. For example, stabilizing rods 14 and 16 will be considerably longer if intended for use in a system for stabilizing four sequential vertebrae in a spine as opposed to stabilizing only two adjacent vertebrae in a spine. Likewise, depending on their intended use, stabilizing rods 14 and 16 can be precontoured along their length. For example, stabilizing rods 14 and 16 can be contoured complementary to the curvature of the portion of the spine to which they will be stabilizing.

As also depicted in FIG. 2, fastener 24 comprises a body 110 having an encircling side wall 112 that extends between a top end face 114 and an opposing bottom end face 116. Radially outwardly projecting from side wall 112 so as to encircle body 110 is a helical thread 118. Recessed on top surface 114 is a polygonal socket 120 adapted to receive a driver. Threads 118 of fastener 24 are configured to threadedly engage with internal threads 40 of collar 22. Accordingly, as depicted in FIG. 5 and as will be discussed below in greater detail, once stabilizing rod 14 is disposed within transverse passage 54 of collar 22, fastener 24 can be screwed into longitudinal passage 38 of collar 22 so that fastener 24 biases stabilizing rod 14 against head 78 of screw 26. In this configuration, stabilizing rod 14 is secured from unwanted movement by being compressed between fastener 24 and head 78 of screw 26. Furthermore, as stabilizing rod 14 pushes against head 78, head 78 is wedged against seat 58 of collar 22, thereby also locking collar 22 relative to screw 26.

Figure 6:
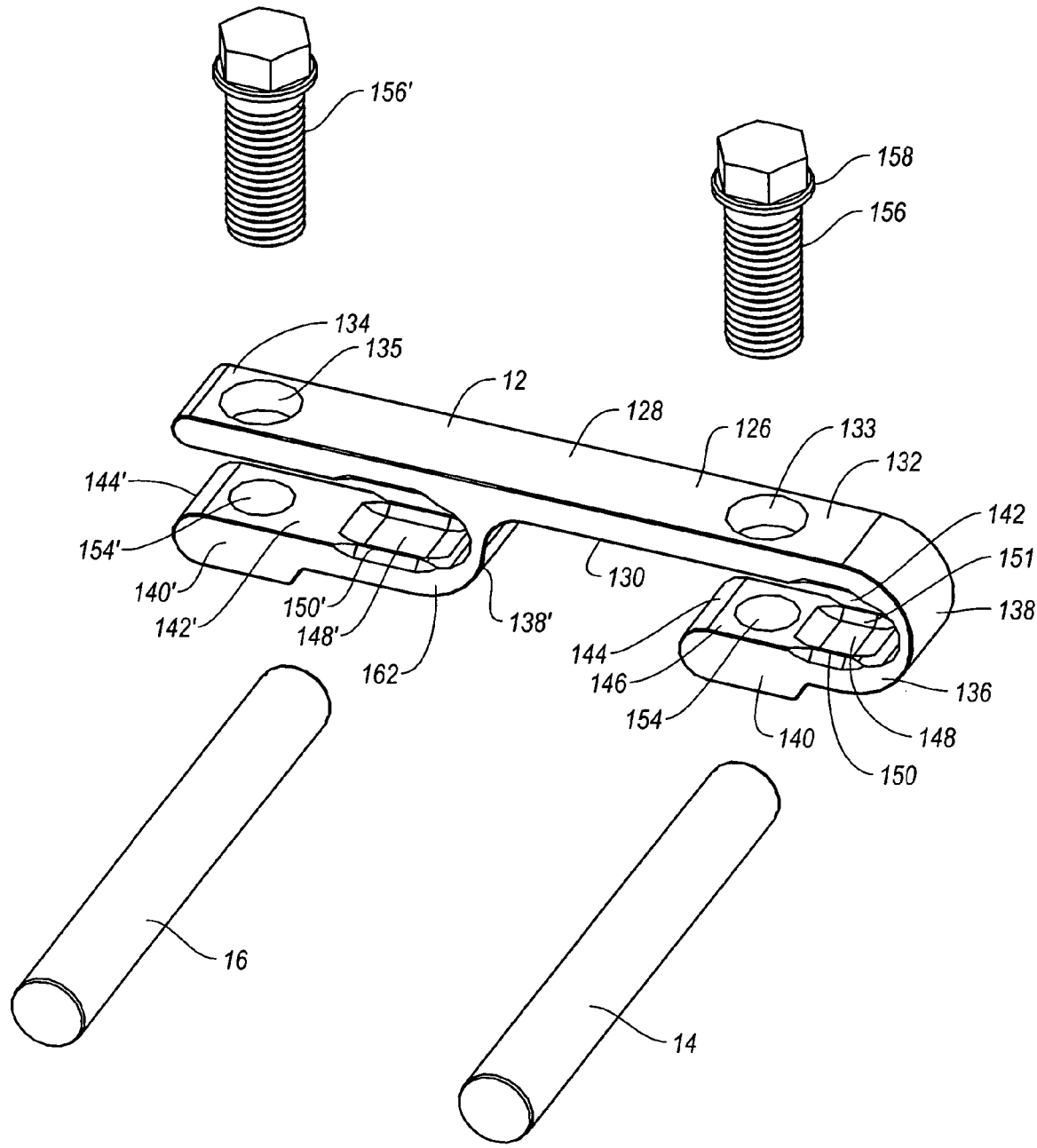
FIG. 6 is an exploded perspective view of the cross link and stabilizing rods of the spinal stabilizing system shown in FIG. 1.

Turning to FIG. 6, cross link 12 comprises a cross bar 126 having a top surface 128 and an opposing bottom surface 130 each extending between a first end 132 and an opposing second end 134. In the embodiment depicted, top surface 128 and bottom surface 130 are substantially flat and are substantially parallel to each other. A first hole 133 extends through cross bar 126 at first end 132 while a second hole 135 extends through cross bar 126 at second end 134. Disposed at first end 132 of cross bar 126 is a first retainer 136. First retainer 136 comprises a first leg 138 that projects downwardly away from bottom surface 130 of cross bar 126 at first end 132 and a second leg 140 that projects from the end of first leg 138 toward second end 134 of cross bar 126 in generally parallel alignment with cross bar 126. First retainer 136 and cross bar 126 combine to form a first slot 142 having a substantially U-shaped configuration with an open mouth 144 formed towards second end 134.

Second leg 140 has an interior surface 146 which in one embodiment can be substantially flat. In the depicted embodiment, however, a pocket 148 is formed on interior surface 146 of second leg 140. As a result of pocket 148, a pair of narrow engagement ridges 150 and 151 is formed on interior surface 146 on opposing sides of pocket 148. Engagement ridges 150 and 151 provide improved biting contact with stabilizing rod 14 so as to improve engagement between cross link 12 and stabilizing rod 14. A similar pocket 148 and engagement ridges 150 and 151 can also be opposingly formed on bottom surface 130 of cross bar 126.

Formed on and/or extending through second leg 140 in alignment with hole 133 is a threaded aperture 154. Once stabilizing rod 14 is positioned within slot 142, a screw 156 is passed down through hole 133 and engaged with threaded aperture 154. Screw 156 has an enlarged head 158 that seats against top surface 128 of cross bar 126 such that by threading screw 156 into aperture 154, stabilizing rod 14 is clamped within slot 142.

A second retainer 162 is also mounted on cross bar 126 so as to project from bottom surface 130 of cross bar 126 at a location between first end 132 and second end 134. Second retainer 162 has substantially the same configuration and component elements as first retainer 130. As such, the same reference characters associated with first retainer 126 with the addition of "'" are used to identify the corresponding elements of second retainer 162. The primary distinction between first retainer 136 and second retainer 162 is that second leg 140' has an extended length. This extended length allows for a tolerance in fit for different spacings for stabilizing rods 14 and 16.

In one embodiment each of the elements of bone stabilizing system 10 is comprised of a metal such as titanium, stainless steel, alloys, or other biocompatible metals. In alternative embodiments, other biocompatible materials such as composites or high strength plastics can also be used. Furthermore, different components of system 10 can be formed from different materials.

Bone stabilizing system 10 will now be discussed with regard to stabilizing a pair of adjacent vertebrae of a spine. Initially, the soft tissue is resected from around the adjacent vertebrae. Two holes are then formed in each vertebrae with each hole extending through a corresponding pedicle of the vertebrae. An anchor 19 that is sized for the corresponding vertebrae is then selected. Second end 74 of screw 26 of anchor 19 is then positioned within the preformed hole and a driver is used to secure screw 25 within the hole in the vertebrae.

Figure 7:
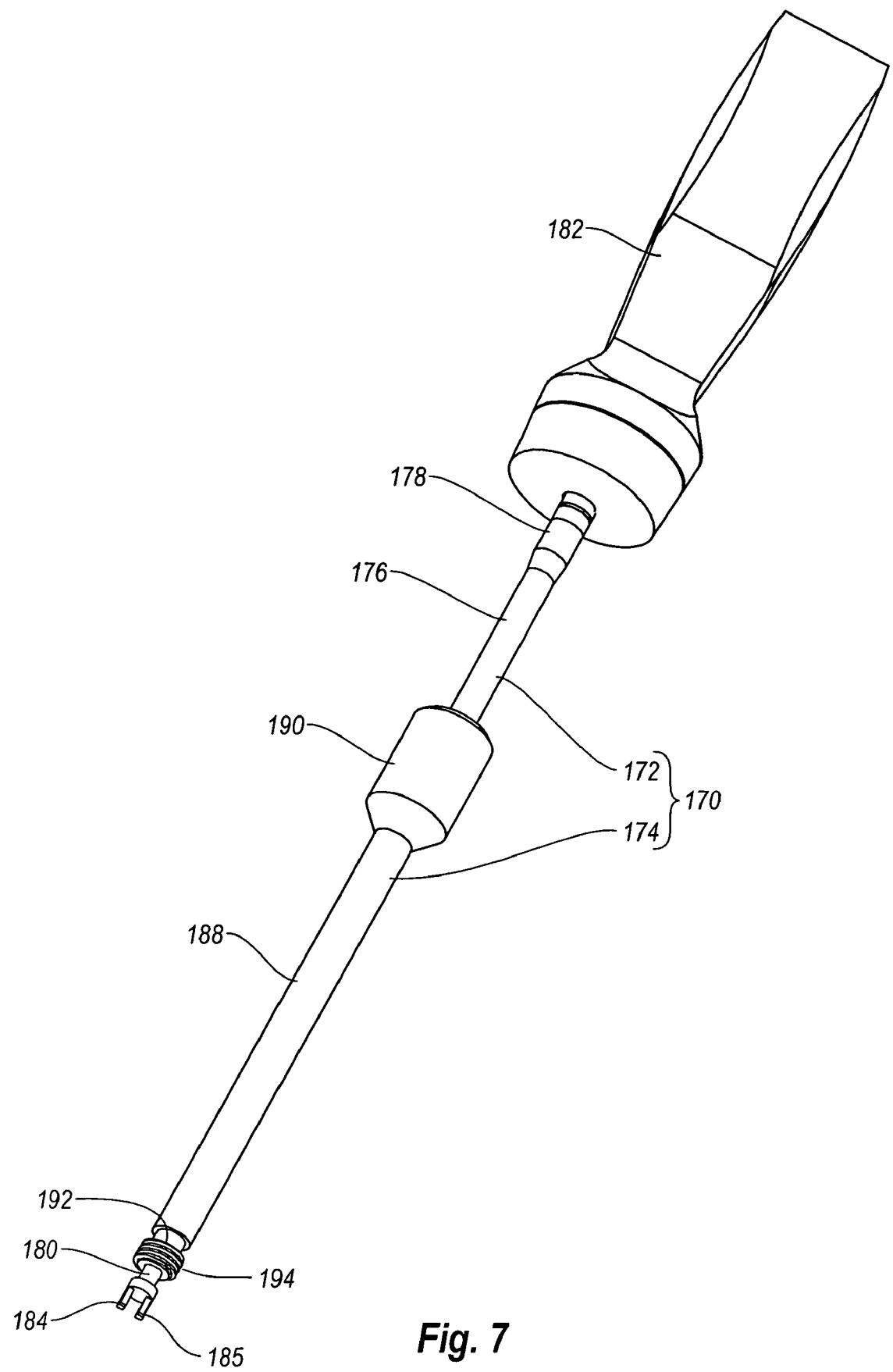
FIG. 7 is a perspective view of a driver assembly.

Depicted in FIG. 7 is one embodiment of a driver assembly 170 that can be used for mounting anchor 19. Driver assembly 170 comprises a driver 172 and a stabilizer 174. Driver 172 comprises an elongated shaft 176 having a first end 178 and opposing second end 180. A handle 182 is mounted at first end 178 while forked prongs 184 and 185 are mounted on second end 180. Stabilizer 174 comprises an elongated sleeve 188 having a first end 190 and an opposing second end 192. Sleeve 188 freely encircles shaft 176 such that sleeve 188 can freely rotate about shaft 176. Encircling and radially outwardly projecting from second end 192 of sleeve 188 is a helical biasing thread 194.

Figure 8:
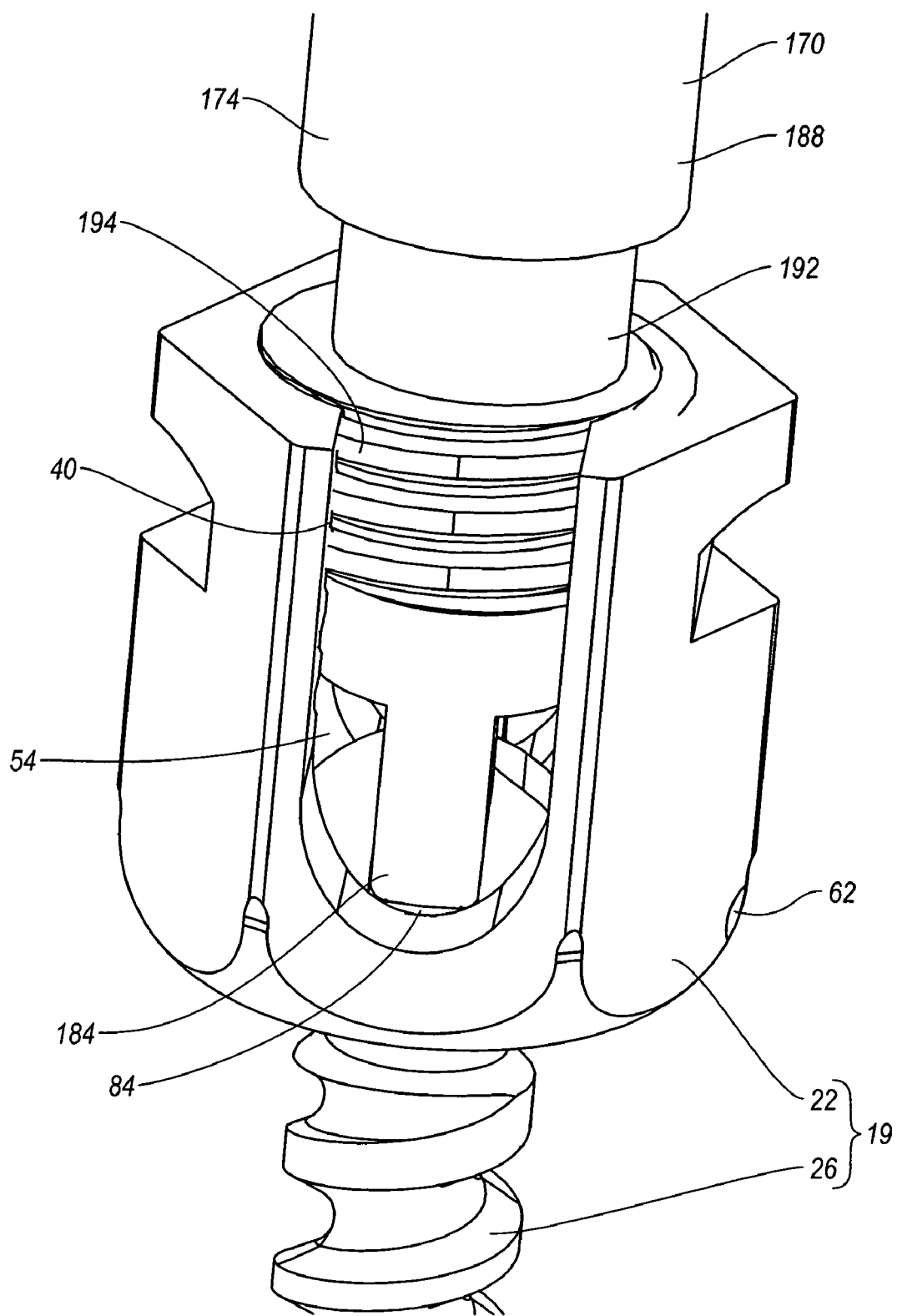
FIG. 8 is an enlarged perspective view of an end of the driver assembly shown in FIG. 7 engaging the anchor of FIG. 1.

Turning to FIG. 8, prior to implanting anchor 19, prongs 184 and 185 are advanced down through collar 22 and are received within engagement slots 84 and 86 on screw 26. In turn, second end 192 of sleeve 188 is also advanced into collar 22. By rotating sleeve 188, biasing threads 194 threadedly engage with internal threads 40 of collar 22, thereby securing stabilizer 174 to collar 22. In this assembled configuration, screw 26 is now held by driver assembly 170 such that screw 26 is prevented from pivoting relative to collar 22. By using driver assembly 170, the surgeon can position the tip of screw 26 into the hole formed in the pedicle of the vertebrae. Screw 26 can then be advanced and secured within the hole by simply rotating handle 182. Once screw 26 is advanced to the desired depth, stabilizer 174 is unscrewed from collar 22 and driver assembly 170 is removed from anchor 19.

As previously discussed, collar 22 is prevented from rotating relative to screw 26 as a result of pin 62. In the present case, this fixed relationship between collar 22 and screw 26 aids in the easy attachment and removal of biasing threaded 194 into and out of collar 22. Furthermore, it is appreciated that driver assembly 170 is only one embodiment of a driver that can be used for mounting anchor 19. In an alternative embodiment, an elongated driver can be used that simply has a socket formed on the end thereof that is complimentary to the exterior surface of collar 22. One example of such a driver is discussed below with regard to FIGS. 9 and 10. Again, because pin 62 prevents rotation of collar 22 relative to screw 26, rotation of the driver that engages collar 22 facilitates rotation of collar 22 which in turns facilitates rotation of screw 26.

This latter described driver is especially useful in situations where it is needed to remove anchor 19 after having been previously implanted. That is, after anchor 19 has been implanted for an extended period of time, soft tissue and/or bone can grow into transverse passage 54 and engagement slots 84 and 86. As a result, attempting to slide prongs 184 and 185 into engagement slots 84 and 86 may require significant time and effort. By using the present embodiment, a driver can simply be slid over first end 34 of collar 22. Rotation of the driver would then facilitate removal of anchor 19 without having to directly engage screw 26. Having collar 22 with the polygonal configuration also aids in the manipulation and use of anchor 19 during minimally invasive procedures.

The above described process is used to mount a separate anchor 19 into each of the holes of the two adjacent vertebrae. As such, an anchor 19 is mounted on the lateral side of each vertebra and the medial side of each vertebra. The two laterally disposed anchors 19 are orientated so that the transverse passages 54 thereof are substantially aligned. The two medially disposed anchors 19 are similarly orientated. First stabilizing rod 14 is then positioned within transverse passages 54 of the two laterally disposed anchors 19 while second stabilizing rod 16 is disposed within transverse passages 54 of the two medially disposed anchors 19. Here it is appreciated that collar 22 of each anchor 19 is free to pivot relative to screw 26 as previously discussed. By pivoting collar 22, stabilizing rods 14 and 16 can be easily received within transverse passage 54 of each collar 22.

Once the stabilizing rods 14 and 16 are positioned, fastener 24 is mounted within first end 34 of each collar 22. As previously discussed, this is accomplished by inserting a driver into socket 120 of fastener 24 and then screwing fastener 24 into first end 34 of collar 22. During the mounting of fastener 24, it is desirable to minimize unwanted torque on collar 22 so as to prevent unwanted movement thereof and prevent unwanted stress on the spine.

Depicted in FIGS. 9 and 10 is one embodiment of an anti-torque device 200 that can be used to minimize toque on collar 22 during mounting of fastener 24. Anti-torque device 200 comprises a tubular sleeve 202 having a first end 204 and an opposing second end 206. Sleeve 202 has an interior surface 208 that bounds the passageway 210 longitudinally extending through sleeve 202. A handle 212 orthogonally projects out from first end 204 of sleeve 202.

Formed at second end 206 of sleeve 202 is an engagement head 214. As depicted in FIG. 10, head 214 at least partially bounds a socket 216 having an interior surface 217 with a configuration complimentary to exterior surface 32 of collar 22. Socket 216 communicates with passageway 210 extending through sleeve 202. Channels 218 and 220 transversely extend through head 214 on opposing sides of socket 216 so that each channel 218 and 220 communicates with socket 216. Channels 218 and 220 are shown having a configuration substantially the same as channels 42 and 44 previously discussed with regard to collar 22. Other designs can also be used.

To prevent unwanted forces on collar 22 and the spine during attachment and tightening of fastener 24, engagement head 214 is advanced over first end 34 of collar 22 so that stabilizing rod 14 is received within channels 218 and 220. In this position, engagement head is directly engaging both collar 22 and stabilizing rod 14. A driver, not shown, having a polygonal end complimentary to socket 120 of fastener 24 is advanced down through passageway 210 of sleeve 202. The driver engages with fastener 24 and is used to rotate fastener 24. Concurrently with rotating fastener 24, the operator applies an opposing resistance force by holding and/or pulling handle 212 of anti-torque device 200. In the depicted embodiment, head 214 is designed to pass over stabilizing rod 14. In alternative embodiments, however, channels 218 and 220 can be eliminated. In this embodiment, head 214 need only extend down to stabilizing rod 14 but not over stabilizing rod 14. This is because engagement head 214 directly engages collar 22 and thus need not engage stabilizing rod 14 to apply the opposing anti-torque force.

Figure 14:
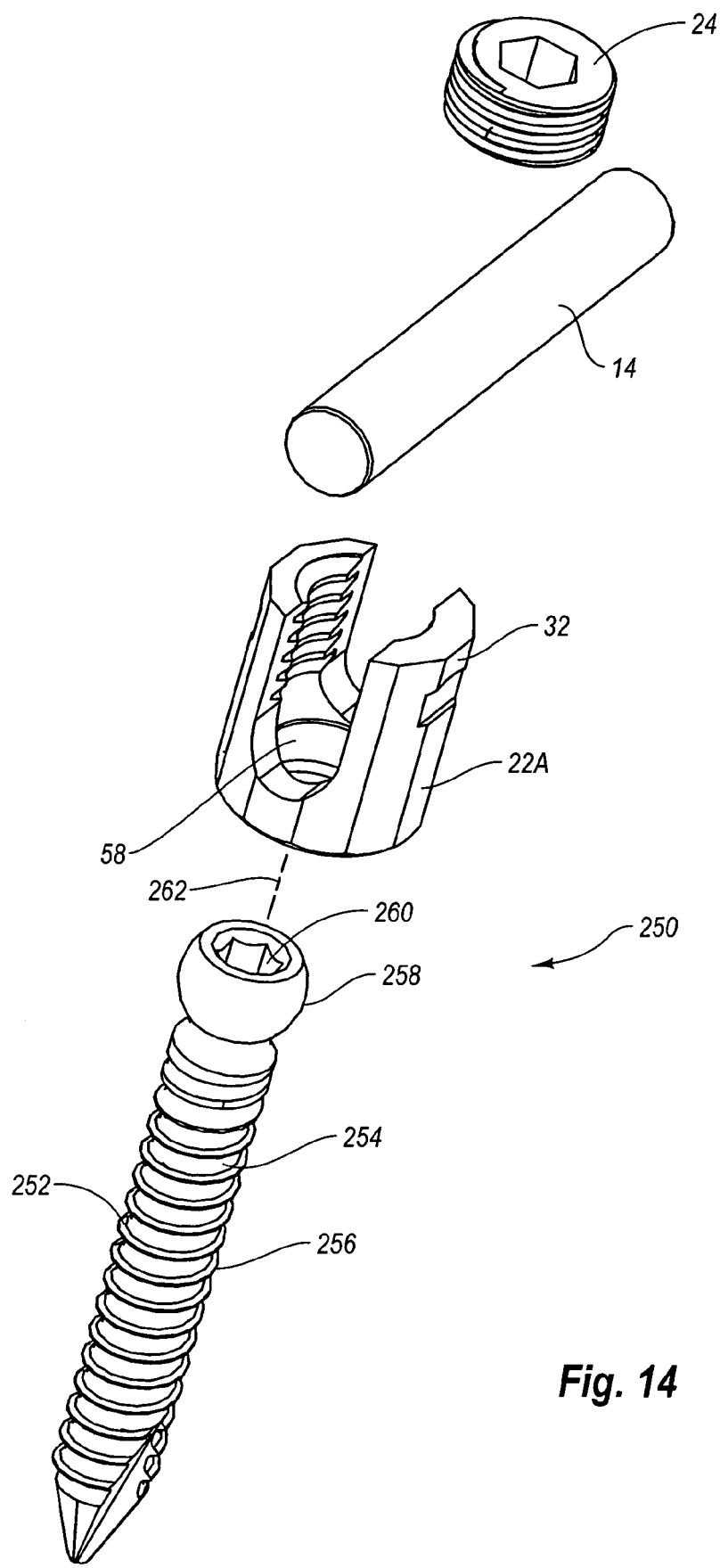
FIG. 14 is an exploded perspective view of an alternative embodiment of a anchor Assembly.

As previously discussed with regard to FIG. 5, as fastener 24 is screwed down into collar 22, stabilizing rod 14 basis against rounded crown 82 of screw 26. It is appreciated that depending upon the placement of screws 26, collars 22 may need to be pivoted out of linear alignment with screws 26 so that stabilizing rod 14 can be positioned within transverse passageway 54 of each anchor 19. As a result of crown 82 being rounded, uniform engagement is formed between stabilizing rod 14 and head 78 independent of the orientation of collar 22. In contrast, if crown 82 were flattened, such as by forming a central aperture on head 78 as depicted in FIG. 14, an asymmetrical force may be applied by stabilizing rod 14 against head 78 tending to further pivot collar 22.

Once fastener 24 is secured within collar 22, anti-torque device 200 and the corresponding driver are removed. This process is then repeated for each of the other anchors 19. Finally, one or more cross links 12 are secured to each of stabilizing rods 14 and 16 so as to prevent lateral movement of stabilizing rods 14 and 16. Specifically, with screws 156 and 156' removed, cross link 12 is simply slid over stabilizing rods 14 and 16 so that stabilizing rods 14 and 16 are received within slots 142 and 142'. Screws 156 and 156' are then passed down through holes 133 and 135 and engaged with threaded apertures 154 and 154', thereby crimping cross link 12 onto stabilizing rods 14 and 16 as shown in FIG. 1. Mounting of bone stabilizing system 10 is then complete.

Figure 11:
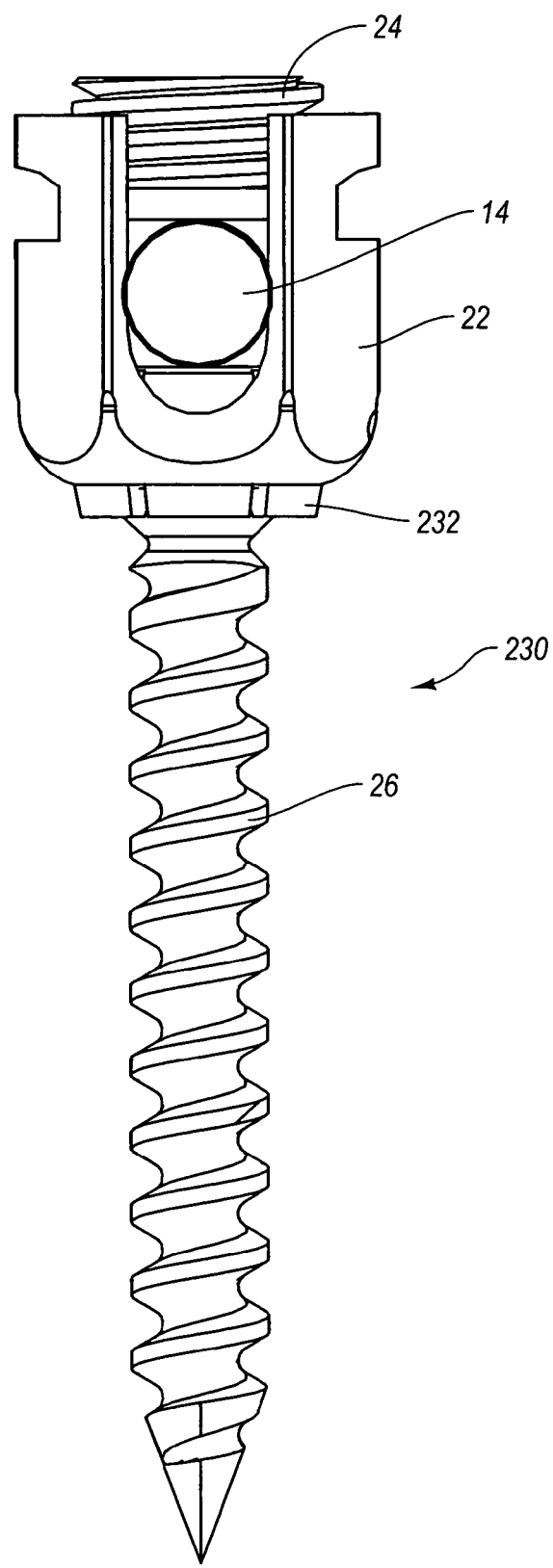
FIG. 11 is a elevated side view of an alternative embodiment of an anchor assembly having a collet.
Figure 12:
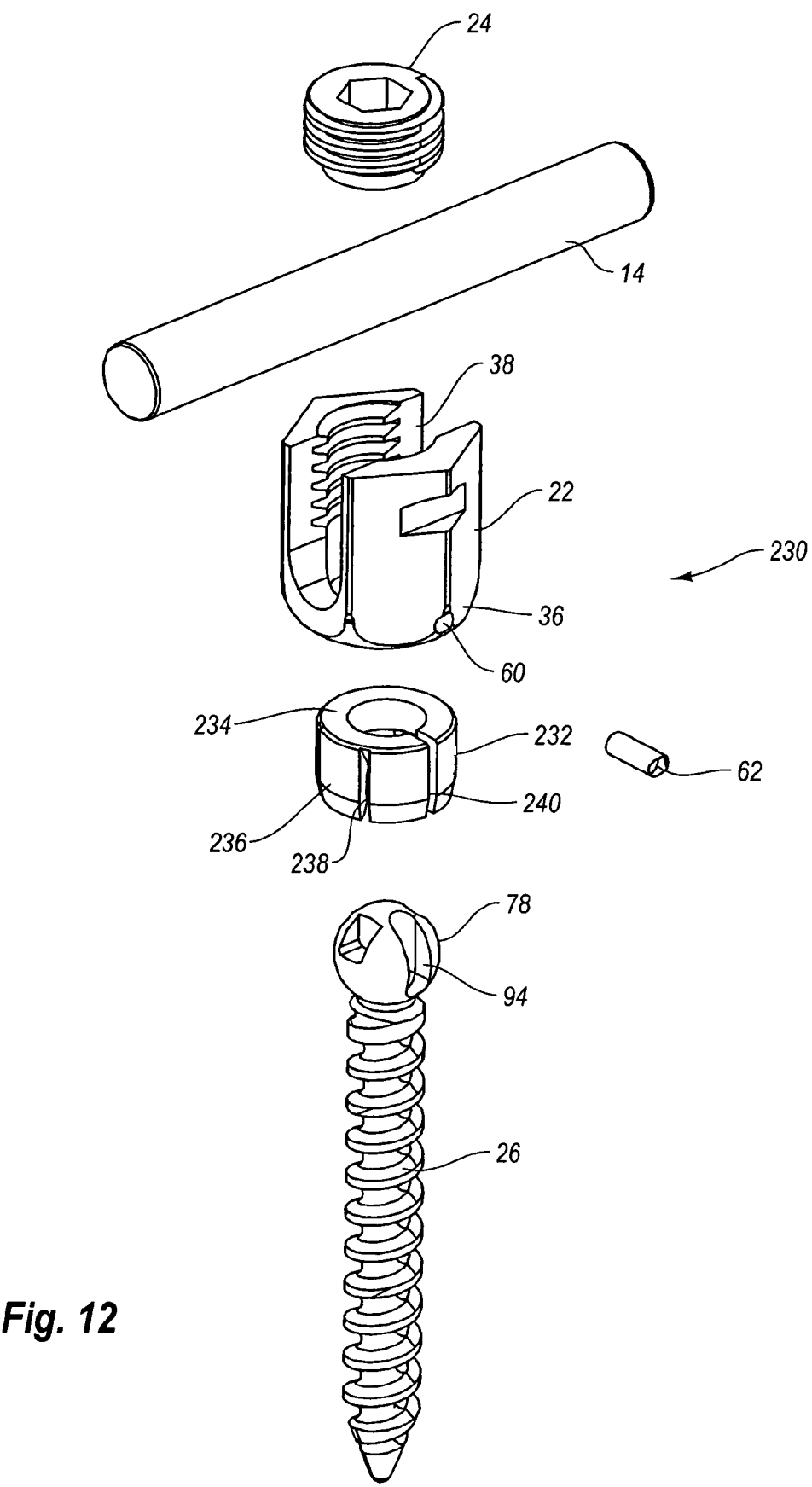
FIG. 12 is an exploded perspective view of the anchor assembly shown in FIG. 11.
Figure 13:
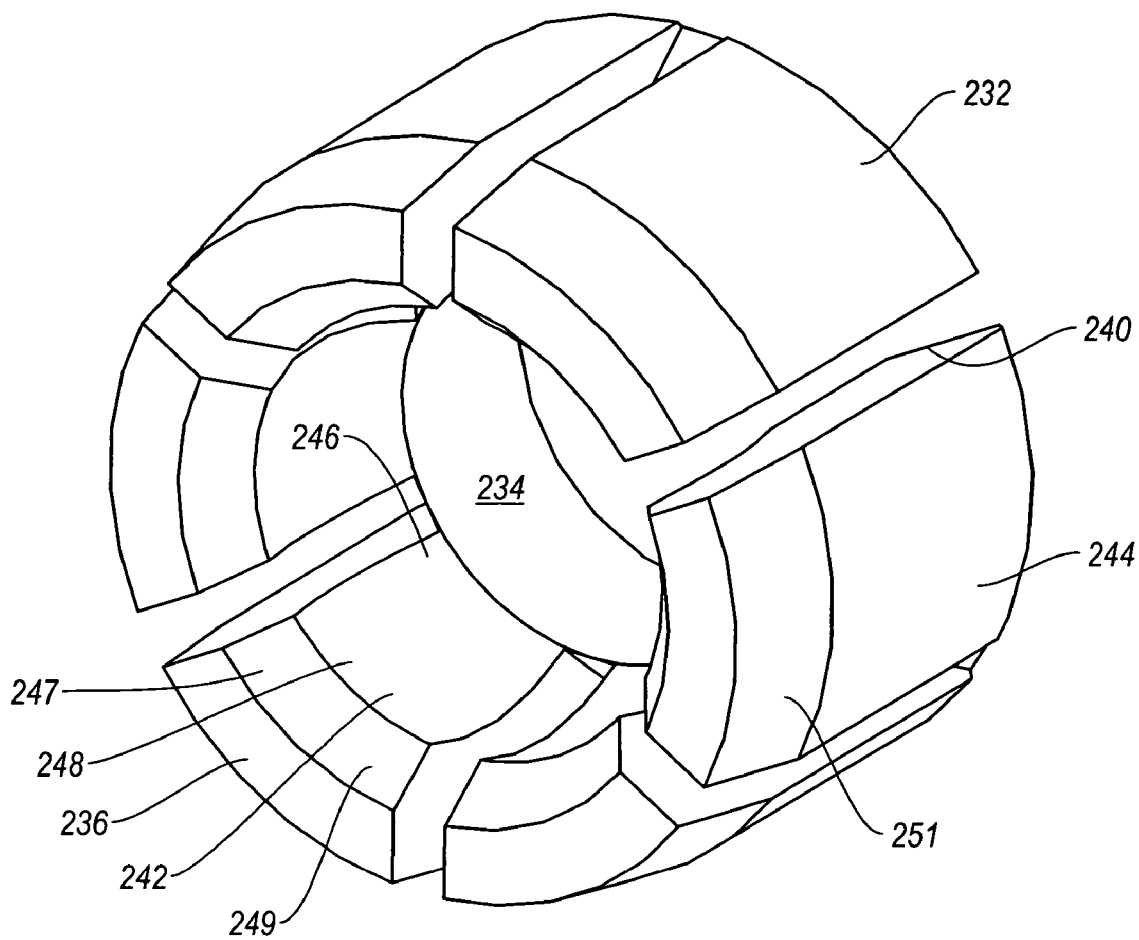
FIG. 13 is a perspective view of the collet of the anchor assembly shown in FIG. 2.

It is appreciated that anchor assembly 18 can come in a variety of different configurations. For example, depicted in FIG. 11 is an alternative embodiment of an anchor assembly 230 incorporating features of the present invention. Common features between anchor assembly 230 and anchor assembly 18 are identified by like reference characters. For example, anchor assembly 230 comprises collar 22, screw 26, and fastener 24. However, in contrast to anchor assembly 18, anchor assembly 230 further comprises an annular collet 232. As depicted in FIGS. 12 and 13, collet 232 comprises an annular ring 234 having a plurality of spaced apart fingers 236 downwardly projecting therefrom. In view of the spacing between fingers 236 a slot 238 is formed between adjacent fingers 236. One slot 240 also extends through ring 234 such that ring 234 has a substantially C-shaped configuration. The formation of slot 240 enables collet 232 to be resiliently constricted for mounting within collar 22.

Each finger 236 has an interior surface 242 and an exterior surface 244 that each extends between a first end 246 and an opposing second end 247. Interior surface 242 comprises a retention portion 248 formed at first end 246 having a concave curvature extending along the length thereof and a concave curvature transversely extending across the width thereof. Interior surface 242 also has a tapered portion 249 formed at second end 248 that slopes radially outward. A radially inwardly sloping tapered portion 251 is also formed on exterior surface 244 at second end 247.

During assembly, collet 232 is radially constricted and then advanced into longitudinal passage 38 of collar 22 from second end 36. As collet 232 is released, it resiliently, radially outwardly extends to it prior configuration so that tapered portion 251 on exterior surface 244 of collet 232 rests against seat 58 (FIG. 6) of collar 22. Head 78 of screw 26 is then pressed into collet 232 so as to seat against retention portions 248 of fingers 236. Any attempts to draw screw 26 out of collet 232 causes fingers 236 to biases against seat 58 of collar 22 which in turn radially constricts fingers 236 so as to further engage head 78, thereby preventing screw 26 from disengaging from collar 22. In this configuration, however, collet 232 and collar 22 can pivot about head 78 of screw 26. Furthermore, if desired, pin 62 can be secured within pin hole 60 of collar 22 so as to pass through slot 240 on collet 232 and rest within locking slot 94. As a result of pin 62, collar 22 would be prevented from rotating relative to screw 26. In alternative embodiments, however, pin 62 can be eliminated and collar 22 can be free to rotate relative to screw 26. During use, stabilizing rod 14 biases against collet 232 as opposed to head 78 of screw 26.

Depicted in FIG. 14 is another alternative embodiment of an anchor assembly 250 incorporating features of the present invention. Like elements between anchor assembly 18 and anchor assembly 250 are identified by like reference characters. Anchor assembly 250 comprises a collar 22A which is substantially identical to collar 22 except that exterior surface 32 thereof has 12 sides as opposed to 6 sides. A screw 252 is shown having a shaft 264 with self-tapping helical thread 256 projecting therefrom. Mounted at the end of shaft 254 is a rounded head 258. Head 260 has a polygonal socket 260 formed on a top end thereof in alignment with the central longitudinal axis 262 of screw 252. Socket 260 is configured to receive a driver for threading screw 252 into bone.

During assembly, screw 252 is advanced down through collar 22A so that head 258 rests against seat 58. As a result, collar 22A can pivot relative to head 258. However, in this embodiment a pin does not extend between collar 22A and head 258, as such collar 22A can freely rotate relative to screw 254. Stabilizing rod 14 and fastener 24 function as with other embodiments. In yet another alternative embodiment, it is appreciated that head 78 of screw 26 shown in the anchor assembly 230 of FIG. 12 can be replaced with head 258 of anchor assembly 250.

Figure 15:
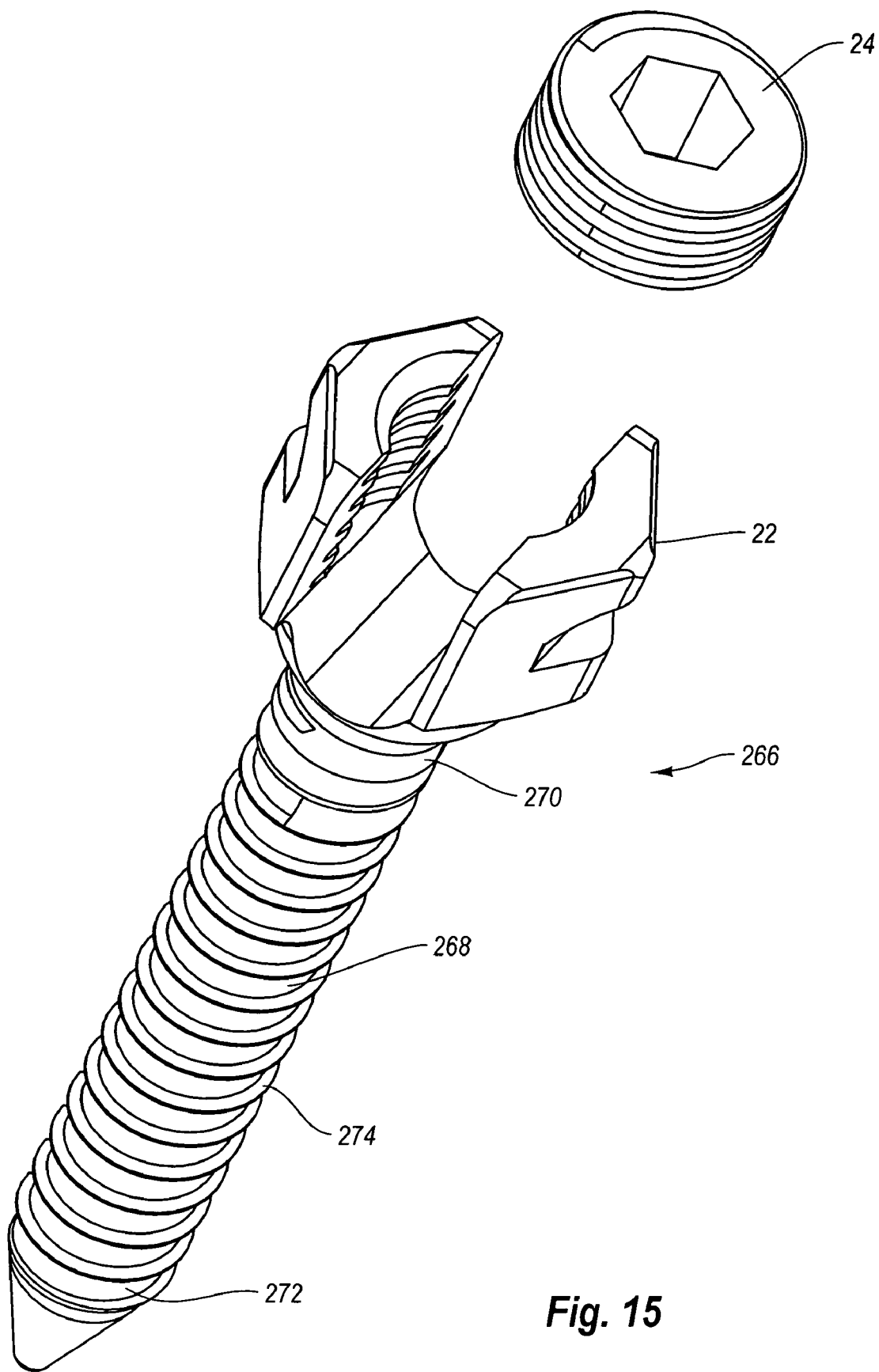
FIG. 15 is a perspective view of another alternative embodiment of an anchor assembly where the collar is integrally formed with the screw.

Finally, depicted in FIG. 15 is still another embodiment of an anchor assembly 266. Anchor assembly 266 substantially comprises collar 22 and screw 26 being integrally formed together with the removal of head 78. Specifically, anchor assembly 266 comprises a shaft 268 having a first end 270 and an opposing second end 272. Helical threads 274 encircles shaft 268 and extend along the length thereof. Collar 22 is integrally formed on first end 270 of shaft 268. As a result, collar 22 cannot pivot or rotate independent of shaft 268. Fastener 24 selectively engages collar 22 as with prior embodiments.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range or equivalency of the claims are to be embraced within their scope.

What is claimed is:

1. A spinal stabilizing system comprising:
   a collar having a central longitudinal axis extending along the length thereof, the collar comprising:
      a tubular sidewall having an interior surface and an exterior surface each extending between a first end and an opposing second end, the interior surface at least partially bounding a longitudinal passage extending therethrough along the central longitudinal axis of the collar;
      a shoulder radially inwardly projecting from the second end of the sidewall so as to at last partially encircle the longitudinal passage and central longitudinal axis of the collar, the shoulder having an interior surface at least partially forming a seat; and
      a pair of spaced apart channels transversely extending through the sidewall at the first end thereof;
   a screw having a threaded portion and an enlarged head mounted on the end thereof, wherein the screw is configured to be received by the collar at the first end of the tubular sidewall, the screw having a central longitudinal axis passing through the head and the threaded portion, the head of the screw resting on or adjacent to the seat of the collar such that the central longitudinal axis of the collar intersects the central longitudinal axis of the screw, the head being freely pivotable relative to the seat so that the central longitudinal axis of the screw can pivot in any 360° direction away from alignment with the central longitudinal axis of the collar; and
   means for locking the screw to the collar so that rotation of the collar about the central longitudinal axis of the collar causes rotation of the screw about the central longitudinal axis of the screw and so that the collar remains freely pivotable relative to the head of the screw during the rotation of the collar.

2. The spinal stabilizing system as recited in claim 1, wherein the exterior surface of the sidewall has a non-circular transverse cross section.

3. The spinal stabilizing system as recited in claim 1, wherein the exterior surface of the sidewall has a polygonal transverse cross section.

4. The spinal stabilizing system as recited in claim 1, further comprising threads formed on the interior surface of the sidewall.

5. The spinal stabilizing system as recited in claim 1, further comprising a fastener removably engaging the interior surface of the sidewall.

6. The spinal stabilizing system as recited in claim 5, further comprising:
the spaced apart channels at least partially bounding a transverse passage that transversely extends through the collar and intersects with the longitudinal passage;
a stabilizing rod disposed within the transverse passage so as to extend through the spaced apart channels; and
the fastener directly biasing against the stabilizing rod so that the stabilizing rod directly biases against the head of the screw.

7. The spinal stabilizing system as recited in claim 1, wherein the means for locking the screw to the collar comprises:
an elongated locking slot longitudinally extending along the exterior surface of the head of the screw; and
a pin being secured to the collar and projecting into the locking slot on the head of the screw.

8. The spinal stabilizing system as recited in claim 7, further comprising a collet disposed between the head of the screw and the seat of the collar.

9. The spinal stabilizing system as recited in claim 1, further comprising a pair of spaced apart engagement slots being formed on the head of the screw, each engagement slot being spaced apart from the central longitudinal axis of the screw.

10. The spinal stabilizing system as recited in claim 1, further comprising an engagement socket having a polygonal transverse cross section formed on the head of the screw, the engagement socket intersecting with the central longitudinal axis of the screw.

11. The spinal stabilizing system as recited in claim 1, wherein the collar can pivot relative to the head of the screw over an angle of at least 10°.

12. A spinal stabilizing system comprising:
a collar having a central longitudinal axis extending along the length thereof, the collar comprising:
a tubular sidewall having an interior surface and an exterior surface each extending between a first end and an opposing second end, the interior surface at least partially bounding a longitudinal passage extending therethrough along the central longitudinal axis of the collar;
a shoulder radially inwardly projecting from the second end of the sidewall so as to at last partially encircle the longitudinal passage and central longitudinal axis of the collar, the shoulder having an interior surface at least partially forming a seat; and
a pair of spaced apart channels transversely extending through the sidewall at the first end thereof;
a screw having a threaded portion and an enlarged head mounted on the end thereof, wherein the screw is configured to be received by the collar at the first end of the tubular sidewall, the screw having a central longitudinal axis passing through the head and the threaded portion, the head of the screw resting against the seat of the collar such that the central longitudinal axis of the collar intersects the central longitudinal axis of the screw, the collar being freely pivotable on the head so that the central longitudinal axis of the screw can pivot in any 360° direction away from alignment with the central longitudinal axis of the collar, an elongated locking slot longitudinally extending along an exterior surface of the head of the screw; and
a pin being secured to the collar and projecting into the locking slot on the head of the screw such that rotation of the collar about the central longitudinal axis of the collar facilitates rotation of the screw about the central longitudinal axis of the screw while the collar remains freely pivotable relative to the head of the screw.

13. The spinal stabilizing system as recited in claim 12, wherein the exterior surface of the sidewall has a non-circular transverse cross section.

14. The spinal stabilizing system as recited in claim 12, wherein the exterior surface of the sidewall comprises a plurality of planar surfaces.

15. The spinal stabilizing system as recited in claim 12, further comprising a fastener threadedly engaging the interior surface of the sidewall.

16. The spinal stabilizing system as recited in claim 15, further comprising:
the spaced apart channels at least partially bounding a transverse passage that transversely extends through the collar and intersects with the longitudinal passage;
a stabilizing rod disposed within the transverse passage so as to extend through the spaced apart channels; and
the fastener directly biasing against the stabilizing rod so that the stabilizing rod directly biases against the head of the screw.

17. The spinal stabilizing system as recited in claim 16, further comprising a cross link mounted on the stabilizing rod, the cross link comprising:
a cross bar having a top surface and an opposing bottom surface that each extend between a first end and an opposing second end;
a first retainer having a first leg that projects downwardly away from the bottom surface of the cross bar at the first end of the cross bar and a second leg that projects from the first leg toward the second end of the cross bar in generally parallel alignment with the cross bar, the first retainer and cross bar bounding a first locking channel, the stabilizing rod being disposed within the first locking channel; and
a second retainer having a first leg that projects down from the bottom surface of the cross bar at a location between the first end and the second end of the cross bar and has a second leg that projects from the first leg toward the second end of the cross bar in generally parallel alignment with the cross bar, the second retainer and cross bar bounding a second locking channel.

18. The spinal stabilizing system as recited in claim 12, further comprising a pair of spaced apart engagement slots being formed on the head of the screw, each engagement slot being spaced apart from the central longitudinal axis of the screw.

19. The spinal stabilizing system as recited in claim 12, wherein the collar can pivot on the head of the screw over an angle of at least 15°.

20. The spinal stabilizing system as recited in claim 12, wherein the elongated locking slot is bounded by a pair of opposing inside faces having a floor formed at one end thereof and a back face formed along the length thereof.

21. The spinal stabilizing system as recited in claim 20, wherein the opposing inside faces are substantially planar.

22. The spinal stabilizing system as recited in claim 12, wherein the elongated locking slot longitudinally extends in parallel alignment with the central longitudinal axis of the screw.

23. A spinal stabilizing system comprising:
a collar comprising:
a tubular sidewall having an interior surface and an exterior surface each extending between a first end and an opposing second end, the interior surface at least partially bounding a longitudinal passage extending therethrough;

a shoulder radially inwardly projecting from the second end of the sidewall so as to at last partially encircle the longitudinal passage, the shoulder having an interior surface at least partially forming a seat; and a pair of spaced apart channels transversely extending through the sidewall at the first end thereof; and a screw wherein the screw is configured to be received by the collar at the first end of the tubular sidewall, comprising:

an elongated shaft having a first end and an opposing second end with a central longitudinal axis extending along the length thereof;

a helical thread encircling the shaft along at least a portion of the length thereof;

a rounded head mounted on the first end of the shaft and having an exterior surface, an elongated locking slot longitudinally extending along an exterior surface of the head in substantially parallel alignment with the central longitudinal axis of the shaft, the head of the screw resting on or adjacent to the seat of the collar so that the collar can universally pivot relative to the head of the screw; and a pin secured to the collar and projecting into the locking slot on the head of the screw so that the collar can still universally pivot relative to the head of the screw.

24. The spinal stabilizing system as recited in claim 23, wherein the exterior surface of the sidewall has a polygonal transverse cross section.

25. The spinal stabilizing system as recited in claim 23, further comprising a fastener removably secured within the longitudinal passage of the collar.

26. The spinal stabilizing system as recited in claim 23, wherein the collar can pivot relative to the head of the screw over an angle of at least 10°.

27. The spinal stabilizing system as recited in claim 23, wherein the exterior surface of the head has a domed, convex curvature.

28. The spinal stabilizing system as recited in claim 23, wherein the head of the screw is substantially spherical.

29. The spinal stabilizing system as recited in claim 23, further comprising a collet disposed between the head of the screw and the seat of the collar.

30. The spinal stabilizing system as recited in claim 23, wherein the exterior surface of the sidewall comprises a plurality of planar surfaces.

31. The spinal stabilizing system as recited in claim 23, further comprising threads formed on the interior surface of the sidewall.

32. The spinal stabilizing system as recited in claim 23, further comprising:

the spaced apart channels at least partially bounding a transverse passage that transversely extends through the collar and intersects with the longitudinal passage;

a stabilizing rod disposed within the transverse passage so as to extend through the spaced apart channels; and a fastener secured to the collar and directly biasing against the stabilizing rod so that the stabilizing rod directly biases against the head of the screw.

33. The spinal stabilizing system as recited in claim 23, further comprising a pair of spaced apart engagement slots being formed on the head of the screw, each engagement slot being spaced apart from a central longitudinal axis of the shaft.

34. The spinal stabilizing system as recited in claim 23, further comprising an engagement socket having a polygonal transverse cross section formed on the head of the screw, the engagement socket intersecting with a central longitudinal axis of the shaft.

35. The spinal stabilizing system as recited in claim 23, wherein the collar can pivot relative to the head of the screw over an angle of at least 15°.

36. The spinal stabilizing system as recited in claim 23, wherein the elongated locking slot is bounded by a pair of opposing inside faces that are each substantially planar.

* * * * *

UNITED STATES PATENT AND TRADEMARK OFFICE
CERTIFICATE OF CORRECTION

PATENT NO.        : 7,691,129 B2
APPLICATION NO.   : 11/254634
DATED             : April 6, 2010
INVENTOR(S)       : Felix It is certified that error appears in the above-identified patent and that said Letters Patent is hereby corrected as shown below:

Title Page
Item 56, Assistant Examiner, change "Sameh Boles" to --Sameh R Boles--
Item 57, ABSTRACT, Right Hand Column, Line 5, change "last" to --least--
Item 57, ABSTRACT, Right Hand Column, Line 14, change "such rotation" to --such that rotation--
Item 56, Page 2, References Cited, U.S. PATENT DOCUMENTS, change
    "7,322,981 B2*    1/2008 Jackson......................606/61" to
    --7,322,981 B2*    1/2008 Jackson......................606/266--
Item 56, Page 2, References Cited, OTHER PUBLICATIONS, change "Biologic & Structural Innovation, *Synergy IQ, Low Back Surgical Technique*, Interpore Cross International, 2003." to --Biological & Structural Innovation, *Synergy IQ, Low Back Surgical Technique*, Interpore Cross International, 2003.--

Drawings
Sheet 14, replace Figure 15 with the figure depicted below, wherein screw 26 has been identified

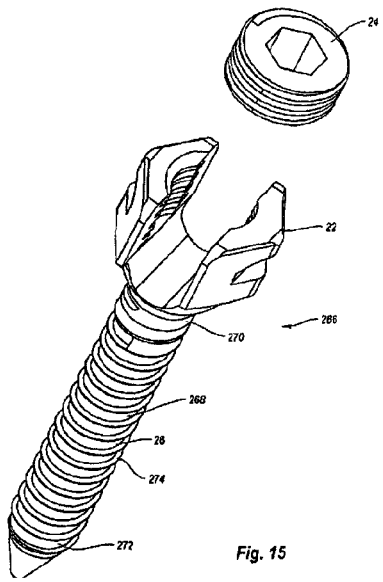

Fig. 15

Signed and Sealed this
Twenty-eighth Day of December, 2010

David J. Kappos
*Director of the United States Patent and Trademark Office*

CERTIFICATE OF CORRECTION (continued)
U.S. Pat. No. 7,691,129 B2

Column 1
Lines 30, 31, and 43, change all three instances of "vertebra" to --vertebrae--
Line 57, change "is" to --it--

Column 2
Line 55, change "a anchor Assembly" to --an anchor assembly--
Line 66, change "spin" to --spine--

Column 4
Line 11, change "side wall 50." to --side wall 28.--
Line 43, change "disposed as" to --disposed in--

Column 5
Line 9, remove the first instance of [by]
Line 13, change "On" to --One--
Line 44, change "surface" to --end face--
Line 63, after "first end 132", insert --,--

Column 6
Line 30, change "first retainer 130." to --first retainer 136.--
Line 31, change "first retainer 130" to --first retainer 136--
Line 38, change "bone" to --spinal--
Line 45, change "Bone" to --Spinal--
Line 54, change "screw 25" to --screw 26--
Line 59, after "and", insert --an--

Column 7
Line 19, change "threaded" to --threads--

Column 8
Line 2, change "toque" to --torque--
Line 25, change "engagement head" to --engagement head 214--
Line 41, change "basis" to --biases--

Column 9
Line 23, change "second end 248" to --second end 247--
Line 34, change "biases" to --bias--
Line 54, change "shaft 264" to --shaft 254--
Line 56, change "Head 260" to --Head 258--
Lines 65-66, change "screw 254" to --screw 252--

Column 10
Line 9, change "encircles" to --encircle--
Line 35, change "last" to --least--

Column 11
Line 46, change "last" to --least--

Column 13
Line 5, change "last" to --least--